United States Patent [19]

Nord

[11] Patent Number: 4,618,324

[45] Date of Patent: Oct. 21, 1986

[54] CENTRI-LEVER ORTHODONTIC APPLIANCE

[76] Inventor: Philip J. Nord, 5213 SE. 30th, No. 210A, Portland, Oreg. 07202

[21] Appl. No.: 695,565

[22] Filed: Jan. 28, 1985

[51] Int. Cl.⁴ ............................................. A61C 7/00
[52] U.S. Cl. ............................................ 433/19
[58] Field of Search ............................ 433/9, 6, 5, 19

[56] References Cited

U.S. PATENT DOCUMENTS 3,618,214  4/1967  Armstrong .
4,382,782  5/1983  Klein et al. .
4,382,783  5/1983  Rosenberg .
4,424,032  1/1984  Howe .
4,462,800  7/1984  Jones .

FOREIGN PATENT DOCUMENTS 374163   7/1921  Fed. Rep. of Germany ........ 433/19
1110363  7/1961  Fed. Rep. of Germany .
1079955  12/1954 France ................................ 433/19

Primary Examiner—Robert Peshock

Attorney, Agent, or Firm—Kolisch, Hartwell & Dickinson

[57] ABSTRACT

A novel intraoral orthodontic appliance for correcting an abnormal jaw condition, or malocclusion, in a patient. The appliance includes an elongate interjaw-force-transferring member having ends which terminate in generally parallel, coplanar closeable loops, with the loops being generally parallel to and spaced apart from the longitudinal axis of the member. A pair of attachment rings are fixed to teeth in different jaws. The loops extend through the attachment rings and are retained therein in a manner providing pivoting of the loops about an axis generally parallel with the plane of the loops. Such construction permits lateral and pivotable movement between the jaws, thereby allowing the patient to eat and speak without interference from the appliance, while still correcting the abnormal jaw condition. The loops may be easily attached to the rings by hooking them on and closing them around the rings with a tool such as a pair of pliers.

6 Claims, 6 Drawing Figures

CENTRI-LEVER ORTHODONTIC APPLIANCE

BACKGROUND AND SUMMARY OF THE INVENTION

The present invention relates to an orthodontic appliance and, more particularly, to an intraoral orthodontic appliance for correcting an abnormal jaw condition, such as overbite or the like.

In orthodontics, the relationship of the upper jaw (maxilla) and the lower jaw (mandible) are of primary importance. The clinically normal condition is referred to as Class I, neutro-occlusion. There are two abnormal conditions or malocclusions referred to as Class II disto-occlusion, commonly called "overbite", and Class III mesio-occlusion. The present invention is directed toward correcting Class II and Class III malocclusions by imparting a corrective force to the abnormally positioned jaw of the patient. In addition to Class II and III malocclusions, the invention may be used for recapturing displaced discs in tempromandibular joint dysfunction.

Conventional interjaw-correcting orthodontic appliances, such as the Herbst appliance, frequently inhibit or prevent lateral, swiveling movement of the jaws, thus interferring with speech, eating and other oral activities. Furthermore, such conventional appliances are subject to frequent breakage, resulting in increased cost and inconvenience for the patient.

Accordingly, it is a general object of the present invention to provide a novel apparatus for correcting Class II and Class III malocclusions which permits lateral, swiveling movement of the jaws while still imparting a corrective force to the affected jaw. By allowing swiveling movement of the jaws, the patient's ability to speak and eat occurs without interference from the appliance. This feature also enhances treatment, by stimulating muscle activity necessary for a new neuromuscular reflex and for proper overall jaw function.

Another object of the present invention is to provide an orthodontic interjaw-correcting apparatus which allows maximum jaw opening.

A further object of the present invention is to provide an orthodontic jaw correcting apparatus which is designed to be "permanently" installed or fixed in the patient's mouth during the treatment period. Such fixed installation better insures patient cooperation, thus shortening treatment time and, concomitantly, reducing the incidence of loss or damage to the appliance.

It is an additional object of the invention to provide an orthodontic, jaw-correcting apparatus which is easy to install and is of simple construction, in order to reduce both installation time and manufacturing costs.

A preferred embodiment of the proposed apparatus of the invention includes a telescope assembly having ends which terminate in generally parallel, coplanar closeable loops, with the loops being generally parallel to and spaced apart from the longitudinal axis of the member. A pair of attachment rings are fixed to teeth on different jaws and extend through the loops, retaining the loops in generally vertical planes. This provides pivoting of the loops about an axis generally parallel with the plane of the loops. The rings are preferably positioned in planes generally normal to the plane of the loops.

In attaching the elongate telescope assembly to the dentition, the open loops are hooked into their corresponding rings and closed around the rings by a dentist or technician using a tool such as a pair of pliers.

With the construction described, it can be seen that the invention provides a lever-like jaw-correcting force to move the affected jaw toward a centric position, while allowing lateral, swiveling movement of the jaws. Furthermore, due to its mechanically simple construction, is easy to install.

These and other objects and advantages of the present invention become more clearly understood from a consideration of the drawings and the following detailed description of a preferred embodiment.

DETAILED DESCRIPTION OF A PREFERRED EMBODIMENT OF THE INVENTION

Figure 1:
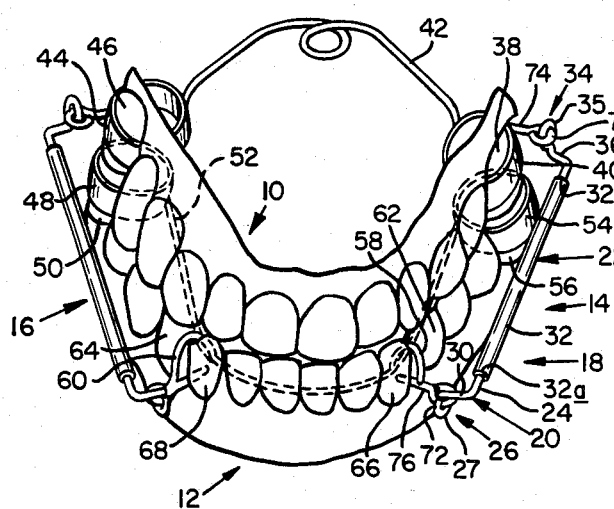
FIG. 1 is an enlarged front perspective view of a pair of the orthodontic appliances of the present invention installed in the closed mouth of a patient.

Referring now to the drawings and, more particularly to FIG. 1, the upper and lower jaws of a patient are shown generally at 10, 12, respectively. Installed on the upper and lower jaws are two intraorally-positionable malocclusion-correcting orthodontic appliances or orthodontic jaw-correcting appliances 14, 16, constructed in accordance with the present invention. The two appliances illustrated are substantial mirror-image duplicates in construction, and such construction will now be described in detail with reference to appliance 14.

Appliance 14 includes an elongate interjaw-force-transferring member or telescope assembly, indicated generally at 18, which comprises a rod member 20 and a sleeve member 22. The construction of assembly 18 is conventional. Obviously, other variations may be used to direct a corrective force to the abnormally-positioned jaw.

Figure 2:
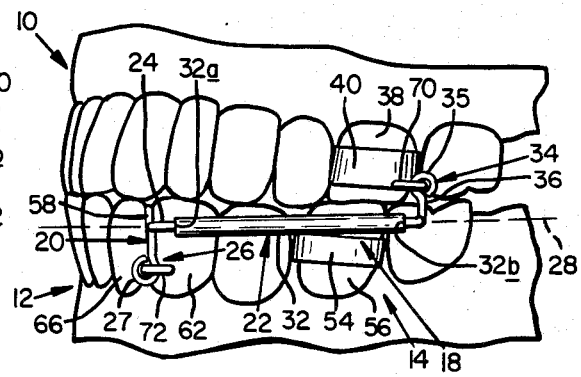
FIG. 2 is an enlarged side view of the closed mouth, showing one of the appliances of FIG. 1.
Figure 3:
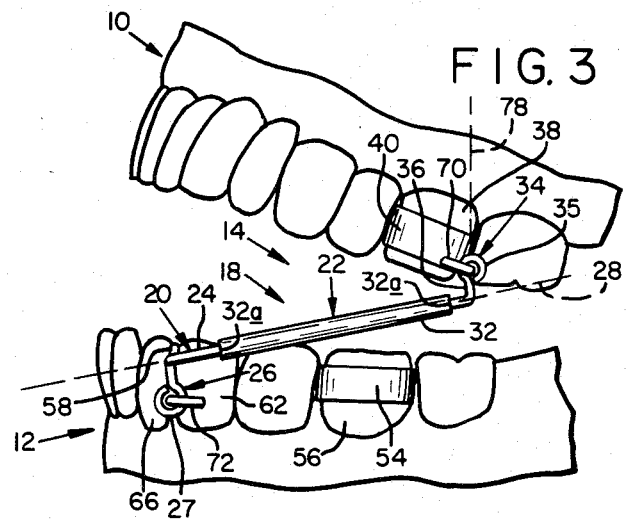
FIG. 3 is a slightly enlarged side view similar to FIG. 2, but with the mouth in an open position.

Referring now also to FIGS. 2 and 3, rod member 20 includes an elongate substantially straight first expanse 24. A second expanse, indicated generally at 26, is disposed at one end of first expanse 24 and terminates in a planar, closeable loop 27, with the plane 37 of the loop being generally parallel to the center line or longitudinal axis 28 of telescope assembly 18 (see FIG. 4). A third expanse 30 joins first expanse 24 and second expanse 26.

Sleeve member 22 of telescope assembly 18 includes an elongate tubular first portion 32 which has an open end 32a and a closed end 32b. Open end 32a of tubular first portion 32 accommodates slidable movement thereinto of first expanse 24 of rod member 20. First expanse 24 and first portion 32 are also collectively referred to as a central portion. A second portion, shown generally at 34, of sleeve member 22, is disposed at closed end 32b of first portion 32 and terminates in a planar, closeable loop 35, with the plane 37 of the loop being generally parallel to longitudinal axis 28 of telescope assembly 18 (see FIG. 4). A third portion 36 joins first portion 32 and second portion 34 of sleeve member 22.

Depending upon the condition sought to be corrected, there are various types of frames that may be used on upper and lower jaws 10, 12. The frame selected for purposes of illustration in FIGS. 1–3 is designed to be used with appliances 14, 16 in the orientations shown in FIGS. 1–3, to correct a Class II malocclusion, or overbite. To correct this condition, an intermaxilliary-force must be applied to move the lower jaw into an anteriorly protrusive position in order to obtain a Class I, or a clinical normal condition. Interjaw-force-transferring member or telescope assembly 18 supplies this directed, corrective force to push the lower jaw forward. Treatment of Class III malocclusions requires the reverse reciprocal affect to protrude the upper jaw and inhibit the lower jaw.

As best seen in FIG. 1, a molar 38 on upper jaw 10 is encircled by a band 40 which is cemented on the surface of the molar. A dental archwire 42 extends along the transversal contour of the hard palate and is connected to a similar band 44 which encircles a molar 46 on the opposite upper dental arch. A band 48 is attached and cemented to a molar 50 on lower jaw 12, below molar 46, as shown. A lingual archwire 52, shown in dashed lines, extends along the inside gum lines of the lower jaw and attaches to a band 54 which encircles and is cemented to a molar 56 on the opposite arch of lower jaw 12. A pair of curved wires 58, 60 extend from archwire 52 between the interproximal space of premolar 62 and canine 66 and premolar 64 and canine 68, respectively.

Appliance 14 is mounted on the teeth by a pair of attachment rings or engaging means 70, 72. Attachment rings 70, 72 are fixed to pins 74, 76, respectively. Pin 76 extends from and is soldered on curved wire 58. Pin 74 is similarly attached to band 40. As shown in FIGS. 2 and 3, rings 70, 72 engage loops 27, 35, respectively, of telescope assembly 18. Rings 70, 72 are generally planarly disposed and are positionable in planes generally normal to the planes of their corresponding loops 27, 35.

Figure 4:
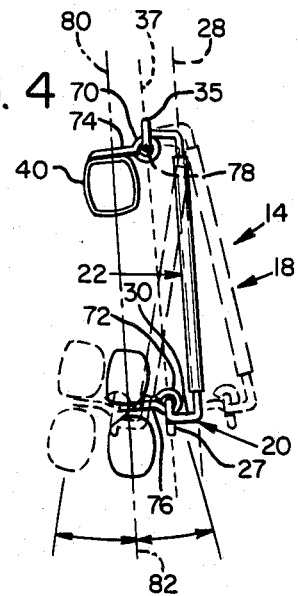
FIG. 4 is a top view of the appliance of the present invention, illustrating in phantom lines the relative pivotable positions of the appliance.

Focusing attention now on FIG. 4, it can be seen that plane 37 of loops 27, 35 is spaced from the longitudinal axis 28 of telescope assembly 18. It can also be appreciated that loops 27, 35, both extending along plane 37, are generally coplanar.

FIG. 2 illustrates the relative position of the appliance when the mouth is closed. In this position, first expanse 24 of rod member 20 is substantially fully received by the first portion of sleeve member 22. Viewing along the plane normal to the view of FIG. 2, and therefore plane 37, containing axis 28, it can be seen that loops 27, 35 are spaced in opposite directions from the plane containing axis 28 of telescope assembly 18. It should also be noted that, in this closed position of the mouth, longitudinal axis 28 of telescope assembly 18 is generally parallel to the sides of the adjacent teeth, and therefore to the dentitions or dental arches (as shown by dentitions 80 (upper jaw) and 82 (lower jaw) in FIG. 4) and to the horizontal plane of the teeth. Another important feature of the appliance, that can best be seen in FIGS. 2 and 3, is the fact that loops 27 and 35, are made of wire and open in a direction away from the central portion of telescope assembly 18. This construction is preferred, because, with the outwardly directed force exerted by the force-transferring member or telescope assembly 18 on rings 70, 72, accidental opening of the loops is eliminated.

FIG. 3 illustrates the telescoping feature of assembly 18. When the mouth is in an open position, first expanse 24 of rod member 20 projects out from sleeve member 22. This telescoping feature allows maximum opening of the jaws.

FIG. 4 demonstrates the lateral, pivotable positions that may be assumed by the jaw due to the unique construction of the present invention. Loops 27, 35 are designed to be engaged by attachment rings 70, 72 in a manner which accommodates lateral and vertical relative movement between the loops and the rings, thus permitting lateral and pivotable movement between the jaws. Loops 27, 35 are pivotable about an axis of revolution, indicated at 78 in FIGS. 3, 4, which is generally parallel with the plane of the loops, and with each of the loops being generally parallel to the dentition. By permitting pivotable movement of the jaws, the patient's ability to carry on oral activities such as speaking and eating occurs without interference from the appliance. It also enhances treatment by stimulating muscle activity necessary for a new neuro-muscular reflex and for proper overall jaw function.

Figure 5:
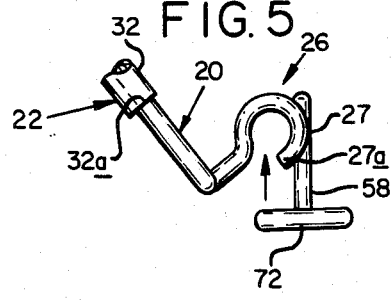
FIG. 5 is a further enlarged side view of a loop employed in the appliance of FIG. 1, in an open position just prior to insertion or hooking into an attachment ring.
Figure 6:
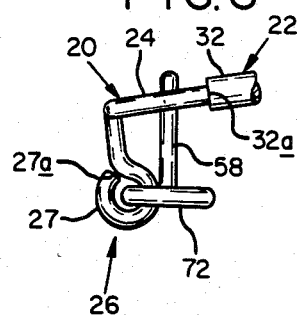
FIG. 6 is a side view similar to FIG. 5, but with the loop in a closed position wherein it has engaged or linked with an attachment ring.

Once the frames are fitted on the patient, appliances 14, 16 are then attached. FIGS. 5 and 6 demonstrate the method of attachment of loops 27, 35 to their corresponding attachment rings 70, 72. The open end 27a of loop 27 is hooked into attachment ring 72. Telescope assembly 18 is then rotated toward molar 38, and, as shown in FIG. 6, the loop is closed around ring 72. Closure of the loop may be easily accomplished by a dentist or technician using a tool such as a pair of pliers. Then, loop 35 is similarly hooked into and closed around ring 70. The same process of attachment is repeated for appliance 16. The proper length of the rod and sleeve members for effecting the desired repositioning of the abnormally-positioned jaw is preselected by making a "wax bite."

From the above disclosure, it can be appreciated that due to the simple construction of appliances 14, 16 they are easily and quickly installed on the dentition of the patient. This results in both decreased installation time and manufacturing costs. Also, because the appliance is designed to be fixed in the patient's mouth and worn continuously, patient cooperation is insured, thereby reducing treatment time and incidence of loss or damage to the appliances.

Many variations are of course possible in the specific, presently preferred form of the invention described above. For example, interjaw-force-transferring member 18 could be curved outwardly from the dentition, rather than straight, thus having a curved center line rather than a longitudinal axis as previously described. The appliance could also be constructed with knobs or disk-shaped ends mounted on pins 74, 76, in place of attachment rings 70, 72 which are presently preferred. Thus, while a particular embodiment of the invention has been described, it should be obvious that variations and modifications are possible without departing from the spirit of the invention.

It is claimed and desired to secure by Letters Patent:

1. An intraoral orthodontic appliance extending between the teeth of the upper jaw and the teeth of the lower jaw comprising:

an elongate extensible-contractable mechanism positioned laterally outwardly of the teeth in the upper and lower jaws, a ring mounted on the lower jaw and a ring mounted on the upper jaw, a first planar loop engaging one of said rings adjacent one end of said mechanism and means mounting said loop on said mechanism with such located laterally inwardly of the mechanism and outwardly of the teeth and in a substantially vertical plane, and a second planar loop engaging the outer ring adjacent the other end of said mechanism and means mounting said second loop on said mechanism with such located laterally inwardly of the mechanism and outwardly of the teeth and in a substantially vertical plane.

2. The appliance of claim 1, wherein one of said loops extends downwardly relative to the mechanism and the other of said loops extends upwardly relative to the mechanism.

3. The appliance of claim 1, wherein one of said rings is mounted on the lower jaw in a relatively forward position in the mouth and the other ring is mounted on the upper jaw in a relatively rearward position in the mouth and said first loop extends downwardly from the mechanism to said one ring and said second loop extends upwardly from the mechanism to said other ring.

4. An orthodontic device for intraoral mounting and malocclusion correction comprising:

an elongate extensible and contractable telescopic mechanism, a first planar loop adjacent one end of said mechanism and means mounting said loop on said one end with the loop laterally spaced from the mechanism and occupying a plane paralleling the axis of the mechanism, and a second planar loop adjacent the other end of the mechanism and means mounting said second loop on said other end of the mechanism with the second loop laterally spaced from the mechanism and occupying a plane paralleling the axis of the mechanism.

5. The device of claim 4, wherein one of said loops extends downwardly relative to said mechanism and the other of said loops extends upwardly relative to said mechanism.

6. The device of claim 4, wherein said loops are malleable, and have a first configuration in which they each have an opening in a side thereof directed away from said elongate telescopic mechanism and are shapeable to a second configuration in which the opening is closed.

* * * * *